US007748387B1

(12) United States Patent
Vu et al.

(10) Patent No.: US 7,748,387 B1
(45) Date of Patent: Jul. 6, 2010

(54) EYE GUARD FOR PROTECTING A PATIENT'S EYES FROM A LASER BEAM DURING SURGERY

(75) Inventors: An Binh Vu, Carlsbad, CA (US); Gregory Philip Jordan, Carlsbad, CA (US)

(73) Assignee: Dupaco, Inc., Oceanside, CA (US)

( * ) Notice: Subject to any disclaimer, the term of this patent is extended or adjusted under 35 U.S.C. 154(b) by 1059 days.

(21) Appl. No.: 11/082,394

(22) Filed: Mar. 17, 2005

(51) Int. Cl.
*A61F 9/00* (2006.01)
(52) U.S. Cl. ............................................. 128/858; 2/15
(58) Field of Classification Search ................. 128/857, 128/858, 846; 2/2, 15, 439, 440; 604/361, 604/362
See application file for complete search history.

(56) References Cited

U.S. PATENT DOCUMENTS

| | | | | |
|---|---|---|---|---|
| 4,122,847 | A | * | 10/1978 | Craig .......................... 128/858 |
| 4,635,625 | A | | 1/1987 | Teeple |
| 4,709,695 | A | * | 12/1987 | Kohn et al. ................. 128/858 |
| 5,151,095 | A | * | 9/1992 | Teeple, Jr. ...................... 606/2 |
| 5,474,063 | A | | 12/1995 | Riendeau |
| 5,927,281 | A | * | 7/1999 | Monteleone et al. ........ 128/858 |
| 6,131,208 | A | * | 10/2000 | Banks ........................... 2/432 |
| 2002/0192829 | A1 | * | 12/2002 | Zainiev et al. ................ 436/39 |
| 2006/0111684 | A1 | * | 5/2006 | Berba et al. ................. 604/361 |
| 2006/0157064 | A1 | * | 7/2006 | Davison et al. ............. 128/858 |

OTHER PUBLICATIONS

Author of Article Balch, K.C. Date: 2000 Publisher: Medicopea International vol. 2000; 18 (1): 10-12 Corneoscleral Protectors and Carbon Dioxide Laser: Safety and Efficacy.*
Sosis, "Evaluation of a New Laser-Resistant Operating Room Drape, Eye Shield, and Anesthesia Circuit Protector", Journal of Clinical Laser Medicine & Surgery, vol. 11, No. 5.
Sosis, et al. "Evaluation of Dermacare Laser Safety System".
Q2 Medical, "Laser Safety System".
Rockwell Laser Industries, "Laser Eyewear", as early as 2002.
Look Eye Garter Total Eye Protection System.
Interactive Optics Inc., "Patient Intra-Ocular Laser Eye Shields", as early as 2002.
Interactive Optics Inc., "Bleph Intra-Ocular Eye Shield", as early as 2002.
Interactive Optics Inc., "Patient Laser Eye Protection", as early as 2002.

* cited by examiner

*Primary Examiner*—Patricia M Bianco
*Assistant Examiner*—Tarla R Patel
(74) *Attorney, Agent, or Firm*—Edward W. Callan

(57) ABSTRACT

A protective eye guard includes a flexible facial mask, a pair of eye covers, a sponge-like material and a layer of shielding material. The facial mask is configured and sized to overlay the portion of a patient's face surrounding the eyes and has a pair of openings overlying the eyes. The eye covers overlie the openings in the facial mask. Within the openings, a pair of enclosed chambers overlying the patient's eyes are defined beneath the respective eye covers. The sponge-like material is disposed in each chamber for absorbing a liquid that disperses and absorbs the energy of a laser beam. The layer of shielding material is an aluminum foil, which is disposed beneath the sponge-like material and overlies the openings for shielding the patient's eyes from the liquid and for also further shielding the patient's eyes from said laser beam.

12 Claims, 2 Drawing Sheets

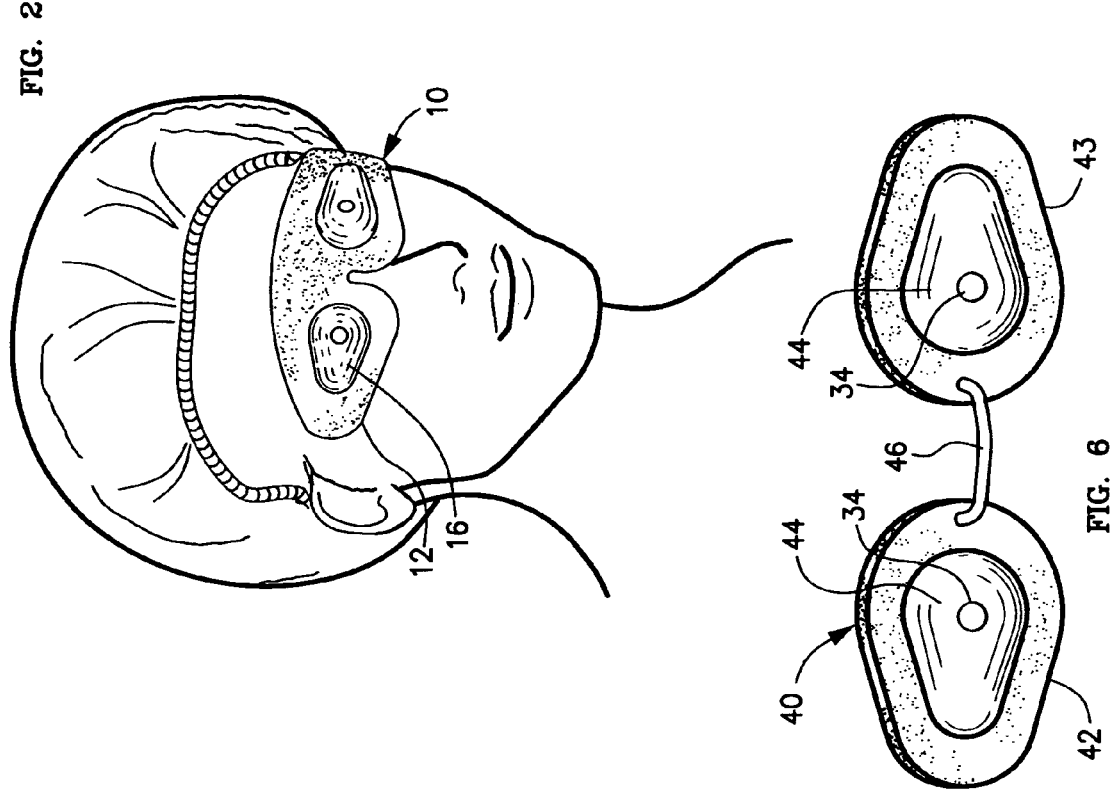
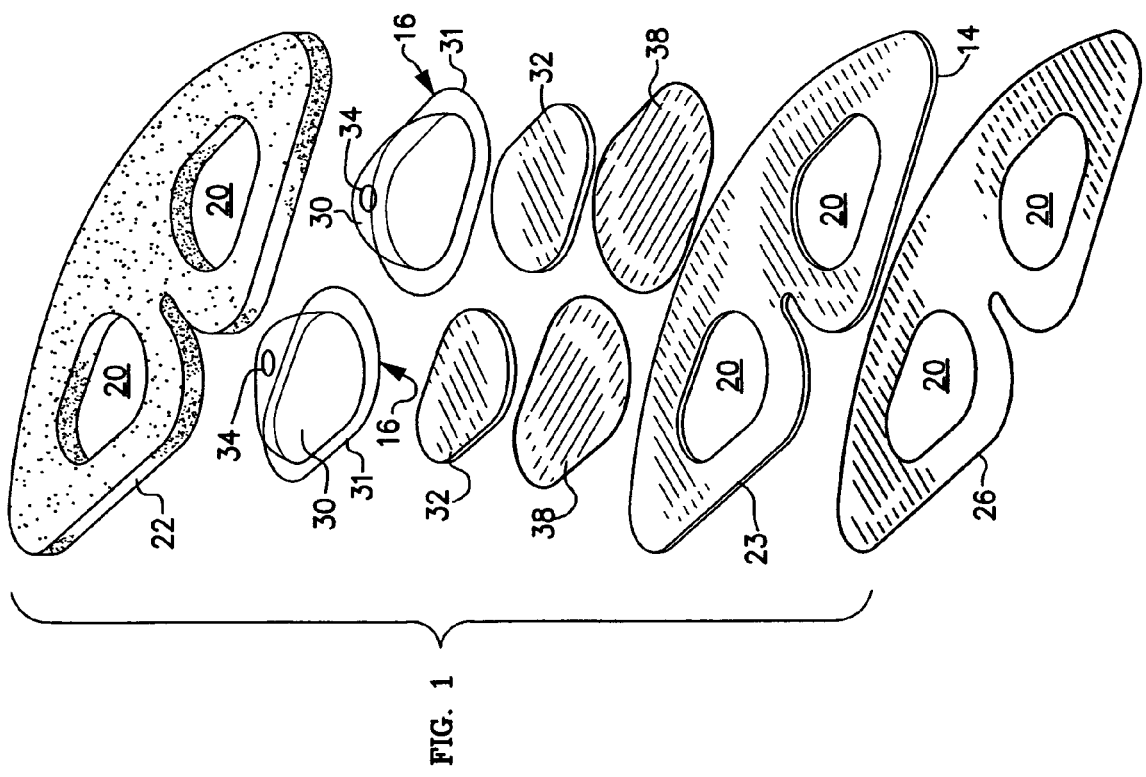

EYE GUARD FOR PROTECTING A PATIENT'S EYES FROM A LASER BEAM DURING SURGERY

BACKGROUND OF THE INVENTION

The present invention generally pertains to protective eye guards and is particularly directed to an improvement to a protective eye guard of the type that is used to protect a patient's eyes from a laser beam during surgery.

Such a protective eye guard is described in U.S. Pat. No. 4,635,625 to Teeple. Such eye guard includes a laser-beam-resistant facial mask configured and sized to overlay the portion of a patient's face surrounding the eyes; a pair of eye pads of moisture absorptive material secured on the inner surface of the facial mask; and an adhesive layer disposed on the inner surface of the periphery of the facial mask for temporarily sealing the facial mask to the face of the patient. The facial mask described in said Teeple patent is made of highly reflective metal foil, such as aluminum foil, and the eye pads are described as being cotton gauze. The laser-beam-resistant facial mask protects a patient's eyes from a laser beam; and the eye pads are moistened with a saline solution to prevent the eyes from drying out during a surgical procedure during which the facial mask is being used.

SUMMARY OF THE INVENTION

The present invention provides a protective eye guard, comprising: a facial mask configured and sized to overlay the portion of a patient's face surrounding at least one of the patient's eyes and having at least one opening overlying said at least one of the eyes when the facial mask surrounds said at least one eye; an eye cover overlying each said opening in the facial mask for protecting said at least one of the patient's eyes from external objects, wherein within each said opening a chamber overlying said at least one of the patient's eyes is defined beneath the cover when the facial mask surrounds said at least one eye; a layer of shielding material overlying each said opening and disposed for shielding said at least one of the patient's eyes from a laser beam; and a sponge-like material disposed in each chamber between the eye cover and the layer of shielding material for absorbing a liquid that disperses and absorbs the energy of a laser beam; wherein the layer of shielding material is disposed for shielding said at least one of the patient's eyes from said liquid.

A sponge-like material is a material that has elastic compressibility and can absorb many times its own weight in liquid.

The present invention also provides a method of protecting a patient's eye(s), comprising the steps of:

(a) covering at least one of the patient's eyes with an eye guard that includes (i) a facial mask configured and sized to overlay the portion of a patient's face surrounding at least one of the patient's eyes and having at least one opening overlying said at least one of the eyes when the facial mask surrounds said at least one eye; (ii) an eye cover overlying each said opening in the facial mask for protecting said at least one of the patient's eyes from external objects, wherein within each said opening a chamber overlying said at least one of the patient's eyes is defined beneath the cover when the facial mask surrounds said at least one eye; (iii) a layer of shielding material overlying each said opening and disposed for shielding said at least one of the patient's eyes from a laser beam; and (iv) a sponge-like material disposed in each chamber between the eye cover and the layer of shielding material;

(b) with the sponge-like material, absorbing a liquid that disperses and absorbs the energy of a laser beam; and (c) with the layer of shielding material, shielding said at least one of the patient's eyes from said liquid.

Additional features of the present invention are described with reference to the detailed description of the preferred embodiments.

BRIEF DESCRIPTION OF THE DRAWING

FIG. 1 is an exploded perspective view of one preferred embodiment of a protective eye guard according to the invention.

FIG. 2 is a perspective view of the protective eye guard shown in FIG. 1 secured to the face of a patient.

In FIG. 5A, the sponge-like material under the eye cover is in a compressed state.

FIG. 6 is a perspective view of an alternative preferred embodiment of the protective eye guard according to the invention.

DETAILED DESCRIPTION

Figure 3:
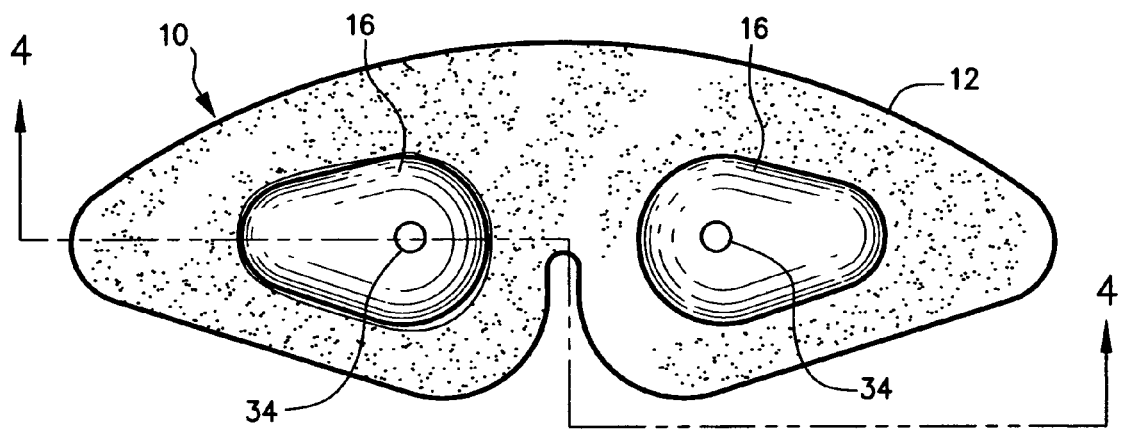
FIG. 3 is a top view of the protective eye guard shown in FIG. 1.

Referring to FIGS. 1-5A, one preferred embodiment of a protective eye guard 10 according to the present invention includes a flexible facial mask 12, an adhesive layer 14 and a pair of eye covers 16.

The flexible facial mask 12 is configured and sized to overlay the portion of a patient's face surrounding the eyes, as shown in FIG. 2, and has a pair of openings 20, which overlie the eyes when the facial mask 12 surrounds the patient's eyes. The facial mask 12 includes a first layer 22 and a second layer 23, both of which are made of a flexible, soft, sponge-like material, such as foamed or expanded synthetic resins, which are soft and resilient. Preferably, the first layer 22 is made of flexible open-cell polyurethane (polyester) or polyethylene. Preferably, the second layer 23 is made of closed-cell polyethylene. The outer and inner surfaces of the second layer 23 are coated with an acrylic adhesive for adhering the outer surface of the second layer 23 to the inner surface of the first layer 22 and for adhering the inner surface of the second layer 23 to a removable paper backing 26.

The acrylic adhesive on the inner surface of the second layer 23 is the adhesive layer 14, which is disposed on the inner surface of the facial mask 12 for temporarily securing the facial mask 12 to the patient's face. The paper backing 26 covers the adhesive layer 14 until the paper backing 26 is removed so that the facial mask 12 can be secured to the patient's face. The adhesive layer 14 must be so disposed as to prevent any substantial openings between the facial mask 12 and the patient's face through which fluid could leak into the patient's eyes, but should not be so tacky or stiff as to be difficult to remove.

The pair of eye covers 16 overlie the openings 20 in the facial mask 12 for protecting the patient's eyes from external objects. A pair of chambers 28 overlying the patient's eyes are defined beneath the respective eye covers 16 when the facial mask 12 is secured to the patient's face.

Each of the eye covers 16 includes a dome 30 and a flange 31 at the periphery of the dome 30. The flange 31 of each eye cover 16 is disposed between the first layer 22 and the second layer 23 of flexible material.

In the preferred embodiments, the eye covers 16 are made of a transparent plastic material, which is preferably somewhat hard or rigid. Some rigidity is important so that the dome 30 is able to withstand pressure from materials or the like which may fall on the dome 30 during a surgical procedure. Preferred transparent plastic materials are Eastman Kodak brand PETG or LEXAN® brand HP FAF polycarbonate film or clear PVC (polychloride). Alternatively, acrylic resins such as LUCITE® polymer or PLEXIGLAS® polymer may be used, as may any plastic material that is transparent, lightweight and rigid enough to withstand at least moderate pressure without collapsing.

Figure 4:
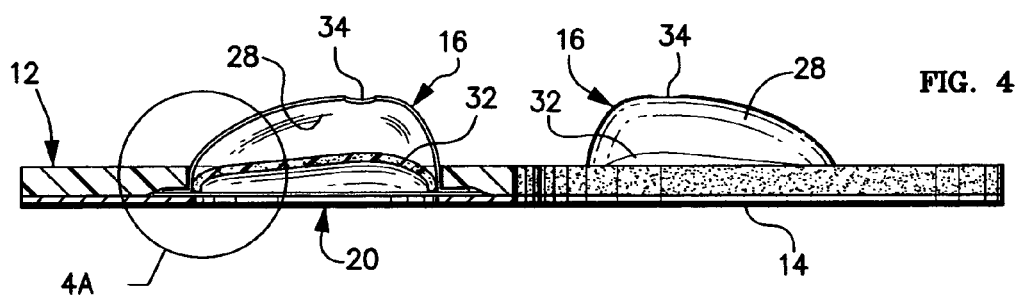
FIG. 4 is a side partial-sectional view of the protective eye guard shown in FIG. 1, with the section being taken along line 4-4 in FIG. 3.
Figure 4A:
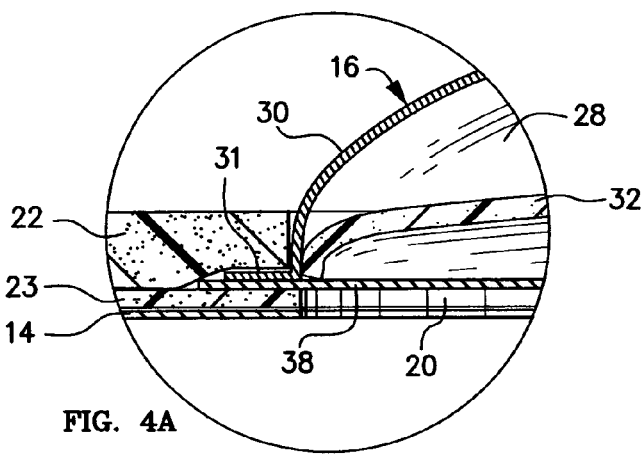
FIG. 4A is an enlarged view of the encircled portion 4A of FIG. 4.

A sponge-like material 32, such as a compressed cellulose sponge, is disposed in each chamber 28 for absorbing a liquid that disperses and absorbs the energy of a laser beam. Initially, the sponge-like material 32 is in a compressed state, as shown in FIGS. 4, 4A and 5. Each piece of sponge-like material 32 is of greater breadth than the chamber 28 and is bent to fit within the chamber 28.

Each eye cover 16 includes an aperture 34 that is disposed for permitting a liquid to be inserted into the chambers 28 for absorption by the sponge-like material 32.

Figure 5B:
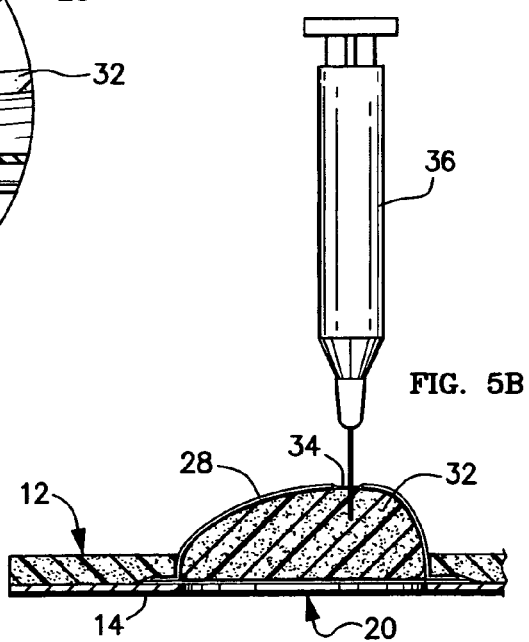
FIG. 5B is the same view as FIG. 5A, except that the sponge-like material under the eye cover is in an expanded state resulting from a fluid having been injected into and absorbed by the sponge-like material.
Figure 5A:
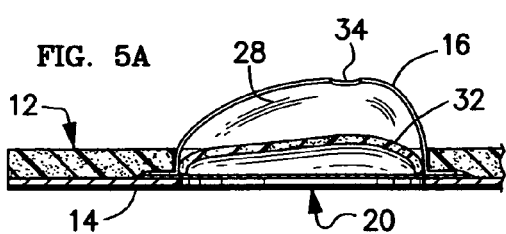
FIG. 5A is the partial-sectional-view portion of FIG. 4.

Referring to FIG. 5B, a syringe 36 is used to insert the liquid into each chamber 28; and the liquid is then absorbed within the sponge-like material 32. Preferably enough liquid is inserted to cause the sponge-like material 32 to expand enough to fill the chamber 28.

Preferably, the liquid is water or a saline solution.

An adhesive-backed material (not shown) may be used to close each aperture 34 after the liquid has been inserted into the chambers 28.

In an alternative embodiment of the protective eye guard (not shown), the eye covers do not include an aperture for permitting a liquid to be inserted into the chambers beneath the covers. In this embodiment, the chambers are enclosed, and a sponge-like material having a laser-beam-absorbing liquid already absorbed therein is disposed within each chamber.

Preferably, the sponge-like material 32 has a characteristic of changing color upon absorbing the liquid. In one embodiment, pigment particles of a different color than the sponge are embedded in the sponge-like material 32. When the sponge-like material 32 absorbs the liquid the liquid reacts with the embedded pigment particles to cause the color of the pigment particles to spread within the sponge-like material 32, whereby the color state of the sponge-like material 32 changes when the sponge-like material 32 absorbs the liquid. In another embodiment in which the sponge-like material 32 does not include pigment particles, the composition of the sponge-like material 32 is such that the color of the sponge-like material 32 changes when the sponge-like material 32 absorbs moisture, such as from pale yellow to bright yellow. A compressed 3M brand yellow cellulose sponge is such a material.

The transparency of the eye covers 16 enables one to observe the state of the sponge-like material 32, and thereby determine whether the sponge-like material 32 is compressed or expanded and/or the color of the sponge-like material 32.

The transparency of the eye covers 16 also enables one to observe when the sponge-like material 32 has absorbed the energy of a laser beam during surgery, whereupon after making such an observation, one may prefer to replace the protective eye guard with a fresh protective eye guard.

A layer of shielding material 38 is disposed beneath the sponge-like material 32. The layer of shielding material 38 overlies the openings 20 for shielding the patient's eyes from liquid within the chambers 28. Each layer of shielding material 38 is of greater breadth than the opening 20 and is disposed between the first layer 22 and the second layer 23 of flexible material. More specifically, the flange 31 of the eye cover 16 is disposed between the first layer 22 and the layer of shielding material 38; and the layer of shielding material 38 is disposed between the flange 31 and the second layer 23. These components 22, 31, 38, 23 are secured to one another by an adhesive.

Although the layer of shielding material is shown in the Drawing as two separate segments 38 respectively overlying the two openings 20, in an alternative embodiment (not shown) the layer of shielding material is a single piece of material that overlies both openings 20.

In the preferred embodiment, the layer of shielding material 38 includes a metallic material for also further shielding the patient's eyes from a laser beam. Preferably the shielding material is a metal foil, such as aluminum foil.

In some alternative embodiments, the layer of shielding material 38 is made of plastic or a textile, such as nylon.

In some alternative embodiments, the eye covers 16 are not made of a transparent material.

In some alternative embodiments (not shown), the eye covers do not include an aperture for permitting a liquid to be inserted into the chambers beneath the covers. In such embodiments, the chambers are enclosed, and a sponge-like material having a laser-beam-absorbing liquid already absorbed therein is disposed within each chamber.

In other respects that are not inconsistent with the foregoing description, the preferred embodiments of a protective eye guard 10, as shown in FIGS. 1-5A are constructed and used in accordance with the disclosure of the aforementioned U.S. Pat. No. 4,122,847, which is incorporated herein by reference thereto.

In still another alternative embodiment, shown in FIG. 6, a protective eye guard 40 according to the present invention includes two flexible facial masks 42 and 43 that are individually configured and sized to overlay the portion of a patient's face surrounding only one the patient's eyes. The facial mask 42 is configured and sized to overlay the portion of a patient's face that surrounds the patient's right eye; and the facial mask 43 is configured and sized to overlay the portion of a patient's face that surrounds the patient's left eye.

Each of the two flexible facial masks 42, 43 has an adhesive layer (not shown) on the inner surface of the mask and is combined with a transparent eye cover 44 in the same manner as described above in relation to the embodiment of FIGS. 1-5A.

The protective eye guard 40 also includes a bridge member 46 that connects the two flexible facial masks 42 and 43. The bridge member 46 is a ductile or malleable material, such as plastic, rubber or aluminum or a similar soft metal or alloy.

In other respects, the protective eye guard 40 is constructed in accordance with one of the above-described embodiments that include a flexible facial mask that is configured and sized to overlay the portion of a patient's face that surrounds both of the eyes.

In further alternative embodiments (not shown), a protective eye guard, as otherwise described above, is configured and sized to overlay a portion of a patient's face that surrounds only one of the patient's eyes.

In still other embodiments the various aspects of the different embodiments described herein are combined with one another to the extent that they are not incompatible with each other.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A protective eye guard, comprising:
    a facial mask configured and sized to overlay the portion of a patient's face surrounding at least one of the patient's eyes and having at least one opening overlying said at least one of the eyes when the facial mask surrounds said at least one eye;
    an eye cover overlying each said opening in the facial mask for protecting said at least one of the patient's eyes from external objects, wherein within each said opening a chamber overlying said at least one of the patient's eyes is defined beneath the cover when the facial mask surrounds said at least one eye;
    a layer of shielding material overlying each said opening and disposed for shielding said at least one of the patient's eyes from a laser beam; and
    a sponge-like material disposed in each chamber between the eye cover and the layer of shielding material for absorbing a liquid that disperses and absorbs the energy of a laser beam;
    wherein the layer of shielding material is disposed for shielding said at least one of the patient's eyes from said liquid.

2. A protective eye guard according to claim 1, wherein each said eye cover includes an aperture disposed for permitting liquid to be inserted into the chamber for absorption by the sponge-like material.

3. A protective eye guard according to claim 2, wherein each eye cover is transparent for enabling one to observe the color of the sponge-like material.

4. A protective eye guard according to claim 3, wherein the sponge-like material has a characteristic of changing color upon absorbing said liquid.

5. A protective eye guard according to claim 1, wherein the facial mask is configured and sized to overlay the portion of a patient's face surrounding only one of the eyes.

6. A protective eye guard according to claim 1, wherein the facial mask is configured and sized to overlay the portion of a patient's face surrounding both of the eyes.

7. A method of protecting a patient's eye(s), comprising the steps of:
    (a) covering at least one of the patient's eyes with an eye guard that includes (i) a facial mask configured and sized to overlay the portion of a patient's face surrounding at least one of the patient's eyes and having at least one opening overlying said at least one of the eyes when the facial mask surrounds said at least one eye; (ii) an eye cover overlying each said opening in the facial mask for protecting said at least one of the patient's eyes from external objects, wherein within each said opening a chamber overlying said at least one of the patient's eyes is defined beneath the cover when the facial mask surrounds said at least one eye; (iii) a layer of shielding material overlying each said opening and disposed for shielding said at least one of the patient's eyes from a laser beam; and (iv) a sponge-like material disposed in each chamber between the eye cover and the layer of shielding material;
    (b) with the sponge-like material, absorbing a liquid that disperses and absorbs the energy of a laser beam; and
    (c) with the layer of shielding material, shielding said at least one of the patient's eyes from said liquid.

8. A method according to claim 7, further comprising the step of:
    (d) through an aperture in each said eye cover, inserting said liquid into the chamber for absorption by the sponge-like material.

9. A method according to claim 8, wherein step (a) comprises the step of:
    (e) covering at least one of the patient's eyes with an eye guard in which each eye cover is transparent for enabling one to observe the color of the sponge-like material.

10. A method according to claim 9, wherein step (a) further comprises the step of:
    (d) covering at least one of the patient's eyes with an eye guard in which the sponge-like material has a characteristic of changing color upon absorbing said liquid.

11. A method according to claim 7, wherein step (a) comprises the step of:
    (d) covering at least one of the patient's eyes with an eye guard in which the facial mask is configured and sized to overlay the portion of a patient's face surrounding only one of the eyes.

12. A method according to claim 7, wherein step (a) comprises the step of:
    (d) covering at least one of the patient's eyes with an eye guard in which the facial mask is configured and sized to overlay the portion of a patient's face surrounding both of the eyes.

* * * * *